United States Patent
Bielenstein et al.

(10) Patent No.: US 10,251,972 B2
(45) Date of Patent: Apr. 9, 2019

(54) COLLAGEN-CONTAINING WOUND DRESSING AND METHOD FOR THE PRODUCTION THEREOF

(71) Applicant: BOTISS BIOMATERIALS GmbH, Zossen (DE)

(72) Inventors: Oliver Bielenstein, Berlin (DE); Drazen Tadic, Berlin (DE)

(73) Assignee: BOTISS BIOMATERIALS GMBH, Zossen (DE)

(*) Notice: Subject to any disclaimer, the term of this patent is extended or adjusted under 35 U.S.C. 154(b) by 0 days.

(21) Appl. No.: 15/553,148

(22) PCT Filed: Jan. 11, 2016

(86) PCT No.: PCT/EP2016/050364
§ 371 (c)(1),
(2) Date: Aug. 23, 2017

(87) PCT Pub. No.: WO2016/134866
PCT Pub. Date: Sep. 1, 2016

(65) Prior Publication Data
US 2018/0071427 A1 Mar. 15, 2018

(30) Foreign Application Priority Data

Feb. 24, 2015 (DE) .................. 10 2015 102 598
Nov. 16, 2015 (DE) .................. 10 2015 119 776

(51) Int. Cl.
*A61F 13/00* (2006.01)
*A61L 15/32* (2006.01)
(Continued)

(52) U.S. Cl.
CPC .......... *A61L 15/325* (2013.01); *A61F 2/2803* (2013.01); *A61F 2/2846* (2013.01);
(Continued)

(58) Field of Classification Search
CPC .......... A61L 27/34; A61L 31/06; A61L 31/10; A61L 27/54; A61L 29/085;
(Continued)

(56) References Cited

U.S. PATENT DOCUMENTS

2016/0067071 A1* 3/2016 Jose .................. A61L 31/005
623/1.15

FOREIGN PATENT DOCUMENTS

JP       2010082146 A      4/2010
WO       2015185597 A2    12/2015
WO    WO 2015185597 A2 * 12/2015 ............. A61L 27/58

OTHER PUBLICATIONS

Officer Nora Lindner, "Translation of the International Preliminary Report on Patentability and the Written Opinion", International Patent Application PCT/EP2016/050364, Report Issued Aug. 29, 2017, 10 pp.
"Decision to Grant" issued in German counterpart patent application No. 102015102598.1, dated Jan. 17, 2017.
(Continued)

*Primary Examiner* — Kim M Lewis
(74) *Attorney, Agent, or Firm* — Kaplan Breyer Schwarz, LLP

(57) ABSTRACT

A wound dressing and a method for production thereof. The wound dressing includes a collagen-containing sheet-like structure, which is made of magnesium or a magnesium alloy. The sheet-like structure has openings and is embedded in a collagen-containing sheet-like structure. The wound dressing is embodied as a geometrically stable bioresorbable membrane and includes a support made of a collagen membrane, on which the collagen-containing sheet-like structure is arranged.

13 Claims, 2 Drawing Sheets

(51) Int. Cl.
*A61L 27/42* (2006.01)
*A61L 27/58* (2006.01)
*A61F 2/28* (2006.01)
*A61L 15/18* (2006.01)
*A61L 15/42* (2006.01)
*A61L 15/64* (2006.01)
*A61F 2/30* (2006.01)
*A61C 8/00* (2006.01)

(52) U.S. Cl.
CPC .............. *A61L 15/18* (2013.01); *A61L 15/42* (2013.01); *A61L 15/425* (2013.01); *A61L 15/64* (2013.01); *A61L 27/427* (2013.01); *A61L 27/58* (2013.01); *A61C 8/00* (2013.01); *A61F 2002/30971* (2013.01); *A61F 2310/00041* (2013.01); *A61F 2310/00371* (2013.01)

(58) Field of Classification Search
CPC ...... A61L 2430/02; A61L 27/26; A61L 27/46; A61L 2300/404; A61L 27/56; A61L 2300/112; A61L 2300/104; A61L 2300/414; A61L 27/58
See application file for complete search history.

(56) References Cited

OTHER PUBLICATIONS

"Office Action" issued in German counterpart patent application No. 102015102598.1, dated Mar. 5, 2015.
"Office Action" issued in German counterpart patent application No. 102015102598.1, dated Apr. 14, 2015.
"Office Action" issued in German counterpart patent application No. 102015102598.1, dated Sep. 13, 2016.
Authorized Officer: Heck, Georg, "International Search Report and Written Opinion" issued in corresponding PCT application No. PCT/EP2016/050364, dated Sep. 1, 2016.
Nan Zhao et al., "Collagen Self-Assembly on Orthopedic Magnesium Biomaterials Surface and Subsequent Bone Cell Attachment", "www.plosone.org", published Oct. 10, 2014, pp. 1-12, vol. 9, No. 10, e110420, Publisher: PLOS One.
Chan Hee Park Ete Al., "Effect on Corrosion Behavior of Collagen Film/Fiber Coated AZ31 Magnesium Alloy", "Digest Journal of Nanomaterials and Biostructures", published Sep. 13, 2013, pp. 1227-1234, vol. 8, No. 3.
Nan Zhao et al., "Endothelialization of Novel Magnesium-Rare Earth Alloys with Fluoride and Collagen Coating", http://www.ncbi.nlm.nih.gov/pmc/articles/PMC4013562/, "International Journal of Molecular Sciences", published Mar. 25, 2014, pp. 1-9, Publisher: MDPI, Published in: CH.

\* cited by examiner

COLLAGEN-CONTAINING WOUND DRESSING AND METHOD FOR THE PRODUCTION THEREOF

FIELD OF THE INVENTION

The invention relates to a collagen-containing implant which is in particular used as a wound dressing. The invention also relates to a method for producing such an implant.

BACKGROUND OF THE INVENTION

Collagen-containing wound dressings are known from practice in various embodiments. For example, in particular non-woven fabric type wound dressings made of a collagen are known, which are produced from a suspension of a native collagen. In contrast to implants made from a chemically dissolved collagen, the former generally have the advantage of exhibiting good flexibility and tear resistance.

Furthermore, wound dressings are available which are produced from donor skin, in particular of animal origin. In particular split-skin graft of porcine origin is used for this purpose, which is prepared by wet-chemical treatment, in particular by acidification and oxidative treatment, in such a manner that essentially a sterile collagen scaffold is remaining. Such wound dressings are in particular used for fire injuries.

A drawback of such known implants is that they are not geometrically stable in the bent state, that is to say depending on the location of application the implant may tend to roll off from the wound or sink into a defect site which is covered by the implant, which is undesirable.

This in particular concerns the use of such collagen implants in the jaw region, where narrow bending radii are needed and the collagen implants are often used to prevent ingrowth of soft tissue into a defect site of a bone, which has previously been filled with a bone graft material.

OBJECT OF THE INVENTION

Given this background, the invention is based on the object of at least mitigating the aforementioned drawbacks of the prior art.

A particular object of the invention is to provide a wound dressing with improved geometric stability, in particular in the bent state.

SUMMARY OF THE INVENTION

The object of the invention is already achieved by a method for producing an implant and by an implant according to any one of the independent claims.

Preferred embodiments and modifications of the invention are specified by the subject matter of the respective dependent claims.

The invention relates to a method for producing an implant which is in particular used as a wound dressing.

According to the invention, a sheet-like structure made of magnesium or of a magnesium alloy is covered with a collagen-containing preparation, and the collagen-containing preparation is dried. In this manner, a composite material comprising collagen and magnesium is produced, in which the collagen at least partly encloses the magnesium.

Sheet-like structure in particular refers to a film, a mesh, a fabric, in particular a non-woven fabric or a knitted fabric. The sheet-like structure in particular has a size of more than half a square centimeter and can be bent by the user. Preferably, a film consisting of magnesium or of a magnesium alloy is used, which may have openings and may in particular be provided in the form of a mesh.

With the magnesium, improved inherent geometric stability of the composite material is achieved. In particular, the latter tends less to sink into covered defect sites. At the same time, magnesium or a magnesium alloy is a bioresorbable material which will decompose within a certain time period after having been placed, that means the implant does not need to be removed after placement.

The covering of the magnesium or magnesium alloy sheet-like structure may be achieved in any suitable manner, in particular by covering the sheet-like structure with the preparation by dipping into the latter, or by pouring or spraying the latter onto the former.

Preferably, a substantially continuous collagen layer is formed by the covering of the magnesium or magnesium alloy sheet-like structure. In particular, a non-woven fabric of collagen is formed after drying.

However, it is also conceivable that only a kind of fluff is formed on the sheet-like structure of magnesium or a magnesium alloy. It is in particular conceivable to use a magnesium or magnesium alloy sheet-like structure which has openings, in particular a sheet-like structure in the form of a mesh. In the latter embodiment variant, the sheet-like structure formed from the collagen suspension would also have openings and would also be in the form of a mesh, since it only covers the magnesium or magnesium alloy scaffold with a fluff. The suspension applied in such a manner may in particular serve as an adhesion promoter for a further layer, in particular a collagen membrane.

The collagen-containing preparation is liquid and solidifies by drying, in particular by lyophilization.

In particular a collagen-containing suspension is used as a collagen-containing preparation. Preferably, a native collagen is used, that means a collagen in which the collagen fibrils have been largely preserved and have not been chemically dissolved. More particularly, a native collagen type I is used. Such a collagen suspension may in particular be produced from a donor skin, preferably of porcine origin. In this case, the skin may be mechanically comminuted, for example by mincing, and is further processed wet-chemically, preferably by an acid treatment and oxidative treatment, so that in particular fat is largely removed and a substantially sterile starting material is remaining.

In particular a collagen suspension with a solids content from 0.5 to 5% (percentages always in percent by weight) is used.

For the acid treatment, hydrochloric acid or phosphoric acid may in particular be used. Preferably, an acid free of chloride ions is used, i.e. in particular phosphoric acid, since otherwise corrosion of the magnesium would be accelerated.

The sheet-like structure of magnesium or of a magnesium alloy as provided according to one embodiment of the invention may have a coating, in particular a passivation layer. It is in particular contemplated to use a sheet-like structure having a magnesium fluoride passivation layer. The latter may be produced by immersing the sheet-like structure into hydrofluoric acid.

The collagen-containing preparation is preferably neutralized, in particular to a pH of greater than 5.5, preferably greater than 6.5, at least prior to covering the magnesium or magnesium alloy sheet-like structure. Thus, the risk for the magnesium or for the passivation layer of dissolving is prevented.

The neutralization is accomplished using a basic buffer, in particular a phosphate buffer, such as trisodium phosphate.

The sheet-like structure made of magnesium or a magnesium alloy may in particular be provided in the form of a mesh. Preferably, the sheet-like structure is provided in the form of a sheet with openings. Compared to a mesh knitted from wires, for example, this results in a better geometric stability.

In particular a magnesium sheet of 20 to 300 µm thickness with openings introduced therein is used as a base material.

The openings serve to provide for an improved bond.

According to one embodiment of the invention, the magnesium or magnesium alloy sheet-like structure is applied onto a support.

In particular a collagen membrane such as, for example, a wet-chemically prepared and lyophilized skin of animal or human origin is employed as a support. In particular a wet-chemically prepared split-skin graft of porcine origin may be used.

Once the magnesium or magnesium alloy sheet-like structure has been applied on the support, the sheet-like structure is preferably covered with the collagen-containing preparation and a composite material of three components is formed. The composite material includes the support; disposed on the support is the collagen non-woven fabric that has been formed by drying the preparation, and the sheet-like structure of magnesium or a magnesium alloy which is embedded in the collagen non-woven fabric and at the same time joined to the support.

In particular by using a collagen-containing suspension it is thus possible to produce a composite in which the sheet-like structure of magnesium or magnesium alloy does not need to be joined to the support by additional means.

However, for improving the cohesion of the composite it is nevertheless conceivable to join the support with the sheet-like structure of magnesium or magnesium alloy by suturing, for example.

Furthermore, the magnesium or magnesium alloy sheet-like structure may have a texture in order to improve the bond, for example in the form of a roughened surface or in the form of small barbs.

However, it is also conceivable to incorporate the sheet-like structure of magnesium or of a magnesium alloy in a kind of pocket. For example, it is in particular possible to prepare a split-skin graft which then consists of upper and lower collagen membranes. The magnesium or magnesium alloy sheet-like structure is inserted into the so formed pocket.

It is also conceivable to arrange the sheet-like structure of magnesium or magnesium alloy between two collagen membranes. In particular it would be possible to form a pocket from two collagen membranes, for example by suturing. This embodiment of the invention does not exclude that before being placed between the collagen membranes the sheet-like structure of magnesium or magnesium alloy is covered by a collagen suspension which then serves as an adhesion promoter to the adjacent membranes. In particular, the sheet-like structure of magnesium or magnesium alloy coated with the collagen suspension is introduced between the two collagen membranes when still being wet, and then the collagen membranes are optionally pressed together and the resulting composite is lyophilized.

The composite material provided by the invention should have a thickness of less than 4 mm, preferably less than 3 mm.

The invention furthermore relates to an implant which can be produced in particular as described above.

The implant comprises a sheet-like structure made of magnesium or of a magnesium alloy. The sheet-like structure is joined to a collagen-containing sheet-like structure, more particularly the magnesium or magnesium alloy sheet-like structure is embedded in the collagen-containing sheet-like structure.

However, it is likewise conceivable that a collagen-containing sheet-like structure is joined to an adjacent magnesium or magnesium alloy sheet-like structure by being sewn or glued thereto, for example. In particular the support as described above could be used, that means a collagen membrane. The membrane could even be joined by interweaving, for example.

The collagen-containing sheet-like structure may in particular be a collagen non-woven fabric which may be prepared as described above by lyophilization of a suspension of a native collagen.

The collagen-containing sheet-like structure may be provided in the form of a continuous layer, but may as well have openings. In particular in the case where a mesh-like magnesium or magnesium alloy sheet material is employed, the latter may merely be covered with a fluff of a collagen non-woven fabric.

In one embodiment of the invention, the implant comprises a support, in particular a support made of a collagen membrane, on which the collagen-containing sheet-like structure is arranged.

The magnesium or magnesium alloy sheet-like structure preferably has openings, at least in sections thereof, and thus is in particular provided in the form of a mesh.

The sheet-like structure of magnesium or of a magnesium alloy preferably has a thickness from 20 µm to 1 mm, most preferably from 50 µm to 300 µm.

The implant in particular has a curved shape and is geometrically stable so as to not sink into defect sites.

BRIEF DESCRIPTION OF THE DRAWINGS

The subject matter of the invention will now be explained in more detail with reference to the drawings of FIGS. 1 to 4.

DETAILED DESCRIPTION OF THE DRAWINGS

Figure 1:
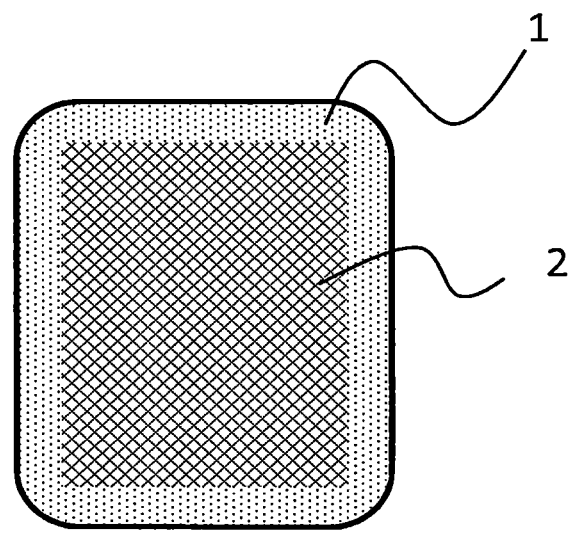
With reference to FIGS. 1 to 3, a way of producing an implant according to the invention will be explained by way of example.

FIG. 1 shows a schematic view of a support 1 which in the present exemplary embodiment consists of a wet-chemically prepared split-skin graft of porcine origin. Thus, this is a collagen membrane.

A sheet-like structure of magnesium or a magnesium alloy 2 has been placed on the support 1.

In this exemplary embodiment, the sheet-like structure is provided in the form of a mesh consisting of a magnesium or magnesium alloy film. In this exemplary embodiment, the mesh has diamond-shaped openings.

The sheet-like structure of magnesium or of a magnesium alloy 2 does not extend as far as to the edge of the support 1.

Figure 2:
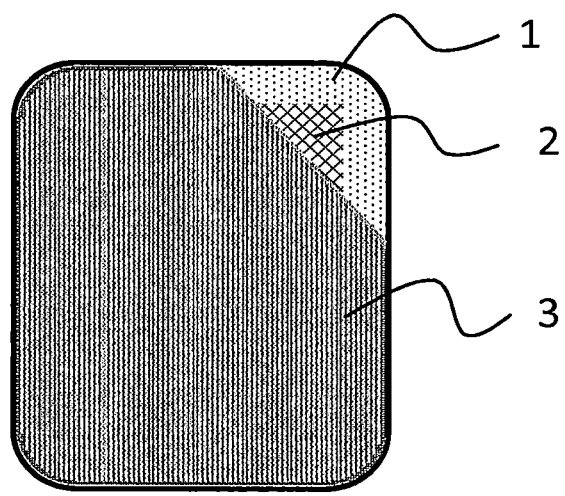

As illustrated in FIG. 2, the support 1 and the sheet-like structure of magnesium or of a magnesium alloy are then covered with a collagen-containing preparation 3.

In the present exemplary embodiment, this is a 0.5 to 5% collagen suspension of porcine origin. The collagen suspension is neutralized using a phosphate buffer before being applied, in particular to a pH value of 7±0.5.

The collagen-containing preparation 3 is then spread with a suitable handling tool.

The so produced composite material is then allowed to rest for a time period between 15 and 120 minutes until the support 1 is well moistened.

Subsequently, lyophilization is performed over a period of 6 hours to 5 days.

Figure 3:
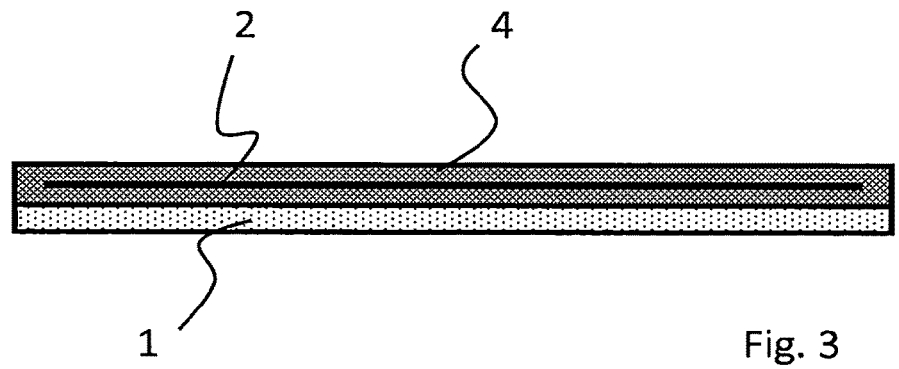

FIG. 3 now shows a schematic sectional view of the produced composite material.

This consists of the support 1, on which the sheet-like structure of magnesium or of a magnesium alloy 2 is now embedded in a collagen non-woven fabric 4 which has been formed from the collagen-containing preparation.

The collagen non-woven fabric 4 at the same time provides a firm bond to the support 1.

Figure 4:
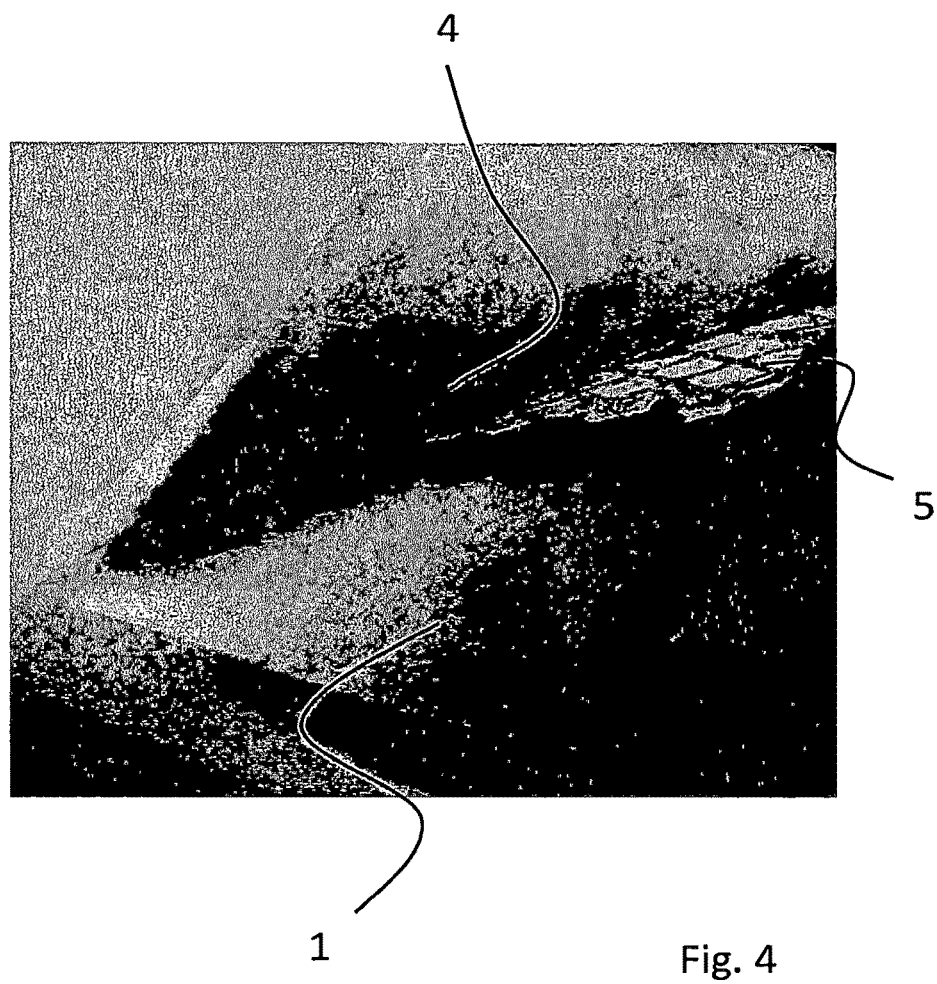
FIG. 4 shows a photograph of an implant.

FIG. 4 is a photograph of a composite material according to the invention, in which the different layers are shown torn apart.

The support in the form of a collagen membrane can be seen, as well as the collagen non-woven fabric 4 torn off therefrom, with a mesh 5 of magnesium embedded therein.

The invention permits to provide, in a straightforward way, a geometrically stable bioresorbable membrane which is particularly suitable, inter alia, for covering defect sites in the bone/jaw region, without tendency of the composite material to sink in.

The invention claimed is:

1. A method for producing a geometrically stable bioresorbable wound dressing membrane, the method comprising:
    covering a sheet-like structure made of magnesium or a magnesium alloy with a collagen-containing preparation;
    drying of the collagen-containing preparation: and applying the sheet-like structure onto a support, wherein the support comprises a collagen membrane.

2. The method for producing the wound dressing membrane of claim 1, wherein the collagen-containing preparation comprises a collagen-containing suspension.

3. The method for producing the wound dressing membrane of claim 2, wherein the suspension includes a native collagen.

4. The method for producing the wound dressing membrane of claim 1, wherein the sheet-like structure comprises a mesh.

5. The method for producing the wound dressing membrane of claim 1, further comprising adjusting the collagen-containing preparation to a pH value of greater than 5.5, at least prior to the covering the sheet-like structure with the collagen-containing preparation.

6. The method for producing the wound dressing membrane of claim 1, wherein the drying of the collagen-containing preparation is performed by lyophilization.

7. The method for producing the implant of claim 1, wherein the support comprises a lyophilized skin of animal or a human origin collagen.

8. A wound dressing comprising:
    a collagen-containing sheet-like structure;
    a sheet-like structure made of magnesium or a magnesium alloy, comprising openings, the sheet-like structure made of the magnesium or the magnesium alloy embedded in the collagen-containing sheet-like structure; and
    a support made of a collagen membrane, on which the collagen-containing sheet-like structure is arranged;
    wherein the wound dressing comprises a geometrically stable bioresorbable membrane.

9. The wound dressing of claim 8, wherein the sheet-like structure made of the magnesium or the magnesium alloy comprises a mesh.

10. The wound dressing of claim 8, wherein the sheet-like structure made of the magnesium or the magnesium alloy has a thickness from 20 µm to 1 mm.

11. The wound dressing of claim 8, wherein the wound dressing is curved.

12. The wound dressing of claim 8, wherein the collagen-containing sheet-like structure comprises a non-woven fabric or a collagen membrane.

13. The wound dressing of claim 8, wherein the sheet-like structure made of the magnesium or the magnesium alloy has a thickness from 50 µm to 300 µm.

* * * * *